US00PP08140P

United States Patent [19]

Apps et al.

[11] Patent Number: Plant 8,140

[45] Date of Patent: Feb. 9, 1993

[54] DAYLILY PLANT NAMED FRAGRANT TREASURE

[75] Inventors: Darrel A. Apps, Chadds Ford, Pa.; Ronald C. Iverson, Barrington, Ill.

[73] Assignee: Iverson Perennial Gardens, Inc., Long Grove, Ill.

[21] Appl. No.: 744,391

[22] Filed: Aug. 13, 1991

[51] Int. Cl.[5] ..... A01H 5/00

[52] U.S. Cl. ..... Plt./87.4

[58] Field of Search ..... Plt./68.1, 87.4

*Primary Examiner*—James R. Feyrer

*Attorney, Agent, or Firm*—Foley & Lardner

[57] ABSTRACT

A new cultivar of daylily plant named Fragrant Treasure, characterized by its large light yellow flowers with ruffled edges and curved shape, fade resistant flowers, very long blooming season in Pennsylvania of from June 15 until October, and by its flowers being open from 6:00 a.m. to 10:00 p.m. in summer after starting to open the previous night.

2 Drawing Sheets

The present invention comprises a new and distinct cultivar of daylily which belongs to the genus Hemerocallis, and is hereinafter referred to by the cultivar name Fragrant Treasure.

Fragrant Treasure is a product of a planned breeding program which had the general objective of creating new daylily cultivars with highly desirable reblooming characteristics, and a stronger, pleasant fragrance.

Fragrant Treasure was originated from a hybridization made by the inventors Darrel A. Apps and Ronald C. Iverson in a controlled breeding program in Chadds Ford, Pa. in 1987. The female parent was the unpatented cultivar Brocaded Gown. The male parent of Fragrant Treasure was the unpatented cultivar HAPPY RETURNS, referred to in more detail below.

Fragrant Treasure was discovered and selected as one flowering plant within the progeny of the stated cross by the inventors on Jun. 10, 1987 in a controlled environment in Chadds Ford, Pa.

The first act of asexual reproduction of Fragrant Treasure was accomplished when divisions were taken from the initial selection on Sep. 1, 1988 in a controlled environment in Chadds Ford, Pa. by the inventors.

Horticultural examination of selected units initiated Jul. 15, 1989 has demonstrated that the combination of characteristics as herein disclosed for Fragrant Treasure are firmly fixed and are retained through successive generations of asexual reproduction.

Fragrant Treasure has not been observed under all possible environmental conditions. The phenotype may vary somewhat with variations in environment such as temperature, light intensity and day length, without, however, any variance in the genotype. The following observations measurements, and comparisons describe plants grown in Chadds Ford, Pa. under field conditions which approximate those generally used in commerical practice.

The following traits have been repeatedly observed and are determined to be basic characteristics of Fragrant Treasure, which in combination distinguish this lily as a new and distinct cultivar:

1. Individual ramets (fans) produce 3–4 flowering scapes in each season;

2. Flowers are highly fragrant, having a generally sweet scent;

3. Mature height of flowering scapes is 22 inches;

4. Individual flowers are 4 inches across, light yellow, ruffled and sun resistant;

5. Individual flowers start to open the evening before, but do not fully open until 6:00 a.m. on the day of flowering and stay open until 10:00 p.m.;

6. Bloom season in Pennsylvania is exceptionally long, starting June 15 and continuing until October;

7. Foliage is approximately 15 inches long;

8. Roots mostly fibrous, but somewhat enlarged on two year fans.

of the many commercial cultivars known to the present inventors, the most similar in comparison to Fragrant Treasure is the male parent, Happy Returns. Happy Returns is primarily characterized by approximately 3 inch fairly intense yellow flowers that have little or no fragrance. In comparison to Happy Returns, Fragrant Treasure has larger flowesr that are a lighter shade of yellow and are much more fragrant.

The accompanying color photographic drawings show typical foliage and flower characteristics of Fragrant Treasure, with colors being as true as possible with illustrations of this type. Sheet 1 is a top perspective view of Fragrant Treasure in an approximately 10 inch pot. Sheet 2 is an enlarged side elevation view, showing the new cultivar more true to size.

In the following description, color references are made to The Royal Horticultural Society Colour Chart.

THE PLANT

Origin: Seedling.

Parentage:

*Seed parent.*—Brocaded Gown.

*Pollen parent.*—Happy Returns.

Classification:

*Botanic.*—Hybrid of genus Hemerocallis.

*Commercial.*—Daylily.

Form: Wide spreading.

Height: Approximately 22 inches.

Growth habit: Clump forming, moderately vigorous.

strength: Moderate.

Foliage:

*Quantity.*—Average.

*Size of leaf.*—15 inches long.

*Shape of leaf.*—Typical Hemerocallis.

*Texture.*—Fine to medium.

*Color.*—Medium to dark green, approximately 139A-B.

Roots:

*Size.*—6 inches long.

*Color.*—Tan.

THE BUD

Form: colunm shape.

Size: $2\frac{3}{4}$ inches long.

Opening: Flat.

Color: Green.

THE FLOWER

Blooming habit: Very long, from early June continuous until October.

Size: 4 inches in diameter.

Borne: Perpendicular to flowering shape, on rigid scape.

Shape: Star.

Petalage:

*number of Petals.*—3 petals, 3 sepals.

*Arrangement.*—Star.

*Color.*—Upper surface: Approximately 4D. Lower surface: Approximately 4D.

*Longevity.*—One day.

*Spotting.*—No markings.

*Curvature.*—Convexly curved toward tip, with tip curled downwardly and inwardly.

*Margin.*—Highly ruffled with longitudinal serration.

Color change: Color is very persistent but may fade slightly in very hot days.

Texture: Crepe-like.

Appearance: Diamond dusted.

Disease resistance: No recognized problems.

Fragrance: Very fragrant.

Lasting quality: One day, 6:00 a.m. to 10:00 a.m.

Flowering: In each growing season individual ramets will produce 3–4 flowering scapes, thereby greatly extending the flowering period.

REPRODUCTIVE ORGANS

Stamens, anthers:

*Arrangement.*—Central, erect.

*Length.*—Tall.

*Number.*—Four.

*Filaments.*—Color approximately 4D.

*Anthers.* —Color approximately 14A.

Pistils: Long.

Stigma: Color, light yellow.

FRUIT

Fertility: Highly fertile.

Shape: Spherical (round).

Color at maturity: Black.

I claim:

1. As new and distinct cultivar of daylily plant named Fragrant Treasure, as illustrated and described.

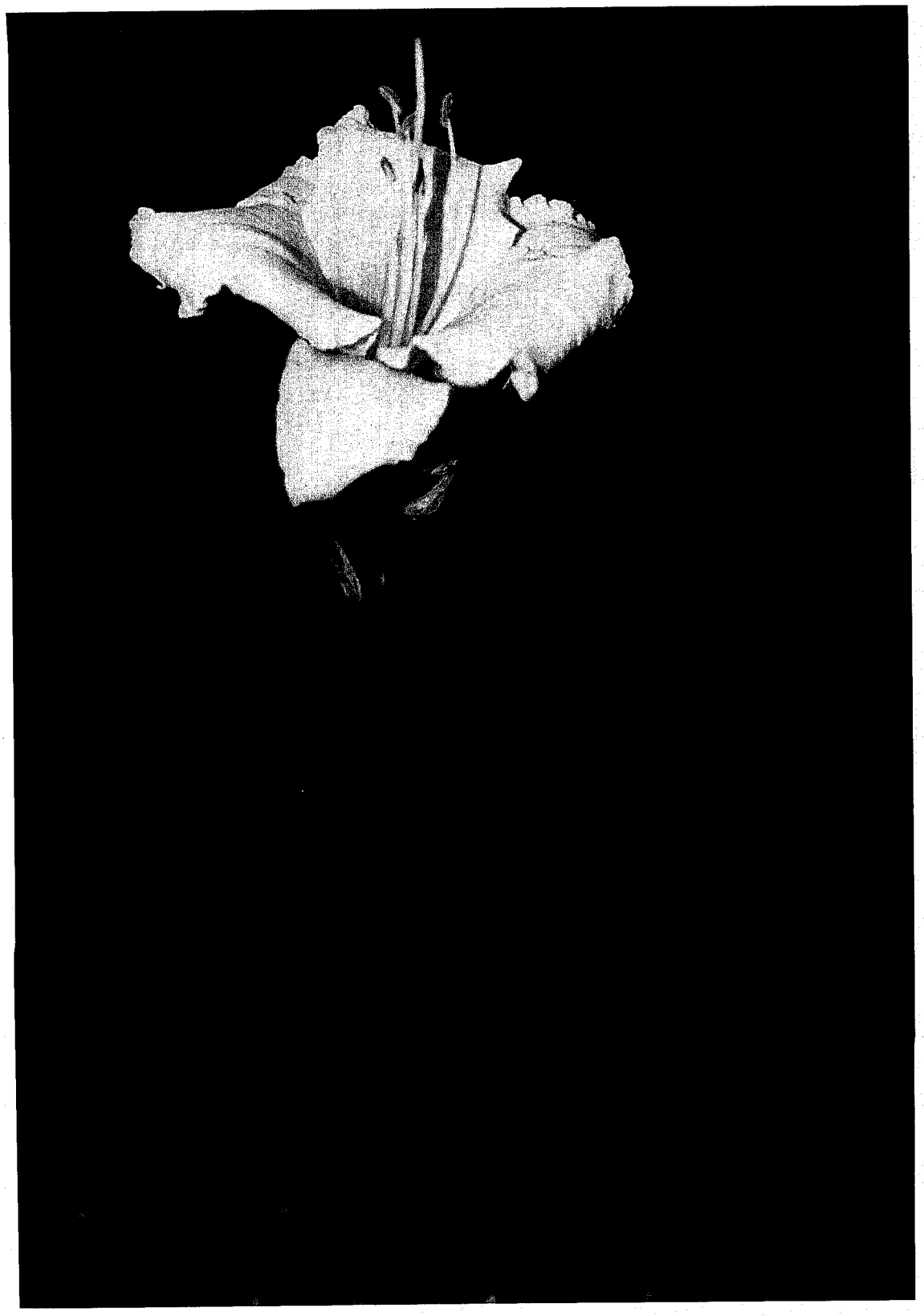

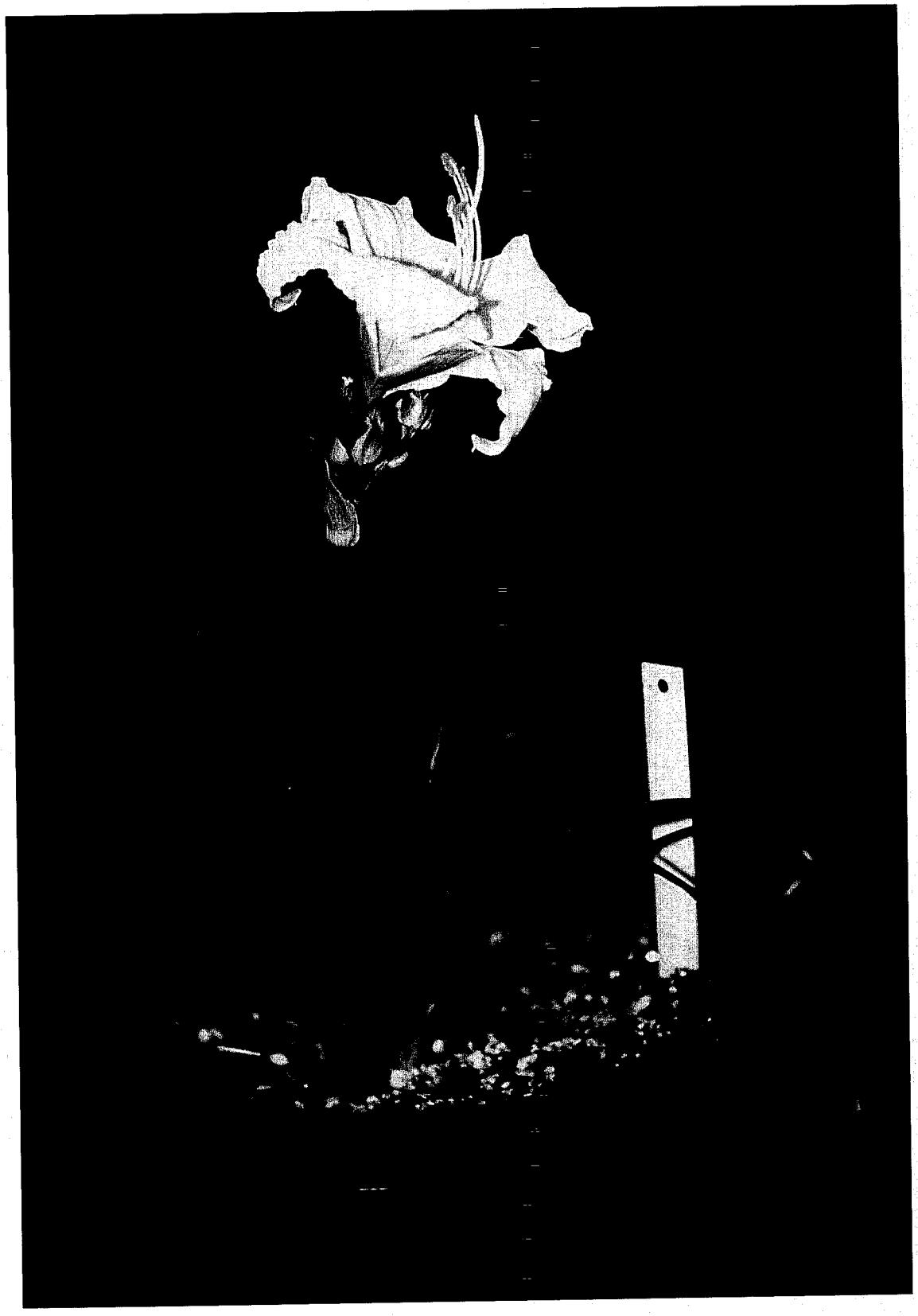

* * * * *